US008927026B2

(12) United States Patent
Dihora et al.

(10) Patent No.: US 8,927,026 B2
(45) Date of Patent: Jan. 6, 2015

(54) SHAMPOO COMPOSITIONS WITH INCREASED DEPOSITION OF POLYACRYLATE MICROCAPSULES

(75) Inventors: Jiten Odhavji Dihora, Hamilton, OH (US); Mark Anthony Brown, Union, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 126 days.

(21) Appl. No.: 13/439,525

(22) Filed: Apr. 4, 2012

(65) Prior Publication Data

US 2012/0276210 A1 Nov. 1, 2012

Related U.S. Application Data

(60) Provisional application No. 61/472,898, filed on Apr. 7, 2011.

(51) Int. Cl.
*A61K 8/11* (2006.01)
*A61K 31/444* (2006.01)
*A61K 8/81* (2006.01)
*A61Q 5/02* (2006.01)
*A61Q 13/00* (2006.01)
*A61K 9/50* (2006.01)
*A61P 17/00* (2006.01)
*A61K 8/73* (2006.01)

(52) U.S. Cl.
CPC . *A61K 8/11* (2013.01); *A61K 8/737* (2013.01); *A61K 8/8158* (2013.01); *A61Q 5/02* (2013.01); A61K 2800/412 (2013.01)
USPC ............................ 424/497; 514/188; 514/119

(58) Field of Classification Search
None
See application file for complete search history.

(56) References Cited

U.S. PATENT DOCUMENTS

| | | | |
|---|---|---|---|
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,730,456 A | 1/1956 | Green et al. |
| 2,730,457 A | 1/1956 | Green et al. |
| 2,800,457 A | 7/1957 | Green et al. |
| 2,800,458 A | 7/1957 | Green |
| 2,809,971 A | 10/1957 | Bernstein et al. |
| 2,826,551 A | 3/1958 | Geen |
| RE24,899 E | 11/1960 | Green |
| 3,236,733 A | 2/1966 | Karsten et al. |
| 3,332,880 A | 7/1967 | Kessler et al. |
| 3,429,827 A | 2/1969 | Ruus |
| 3,516,941 A | 6/1970 | Matson |
| 3,660,304 A | 5/1972 | Matsukawa et al. |
| 3,681,248 A | 8/1972 | Gould et al. |
| 3,691,140 A | 9/1972 | Silver |
| 3,753,196 A | 8/1973 | Kurtz et al. |
| 3,761,418 A | 9/1973 | Parran, Jr. |
| 3,772,215 A | 11/1973 | Gould et al. |
| 3,826,756 A | 7/1974 | Bachmann et al. |
| 3,886,085 A | 5/1975 | Kiritani et al. |
| 3,898,039 A | 8/1975 | Lin |
| 3,929,678 A | 12/1975 | Laughlin et al. |
| 3,958,581 A | 5/1976 | Abegg et al. |
| 3,962,418 A | 6/1976 | Birkofer |
| 3,964,500 A | 6/1976 | Drakoff |
| 3,965,033 A | 6/1976 | Matsukawa et al. |
| 4,001,140 A | 1/1977 | Foris et al. |
| 4,046,750 A | 9/1977 | Rembaum |
| 4,062,799 A | 12/1977 | Matsukawa et al. |
| 4,075,134 A | 2/1978 | Morehouse, Jr. et al. |
| 4,081,376 A | 3/1978 | Strub |
| 4,087,376 A | 5/1978 | Foris et al. |
| 4,089,802 A | 5/1978 | Foris et al. |
| 4,093,556 A | 6/1978 | Wojciak |
| 4,100,103 A | 7/1978 | Foris et al. |
| 4,105,823 A | 8/1978 | Hasler et al. |
| 4,145,184 A | 3/1979 | Brain et al. |
| 4,166,152 A | 8/1979 | Baker et al. |
| 4,183,911 A | 1/1980 | Smithies et al. |
| 4,197,346 A | 4/1980 | Stevens |
| 4,197,865 A | 4/1980 | Jacquet et al. |
| 4,217,914 A | 8/1980 | Jacquet et al. |
| 4,221,710 A | 9/1980 | Hoshi et al. |
| 4,234,627 A | 11/1980 | Schilling |
| 4,240,450 A | 12/1980 | Grollier et al. |
| 4,247,411 A | 1/1981 | Vanierberghe et al. |

(Continued)

FOREIGN PATENT DOCUMENTS

| | | |
|---|---|---|
| CA | 2306397 A1 | 10/2000 |
| CN | 101088567 | 12/2007 |

(Continued)

OTHER PUBLICATIONS

U.S. Appl. No. 14/032,835, filed Sep. 20, 2013, Dihora et al.
U.S. Appl. No. 14/032,859, filed Sep. 20, 2013, Dihora et al.
U.S. Appl. No. 14/032,868, filed Sep. 20, 2013, Cetti et al.
U.S. Appl. No. 14/032,888, filed Sep. 20, 2013, Li et al.
U.S. Appl. No. 14/045,661, filed Oct. 3, 2013, Dihora et al.
U.S. Appl. No. 14/045,670, filed Oct. 3, 2013, Dihora et al.
Herbig—"Encapsulation" Kirk Othmer Encyclopedia of Chemical Technology, V.13, Second Edition, pp. 436-456.
Zim's Crack Creme (R), 2003, Perfecta Products, Inc., Berlin Center, Ohio 44401.
PCT International Search Report and Written Opinion dated Nov. 27, 2012, PCT/US2012/032076.

(Continued)

*Primary Examiner* — Robert A Wax
*Assistant Examiner* — William Craigo
(74) *Attorney, Agent, or Firm* — Carlos A. Garcia; James T. Fondriest

(57) ABSTRACT

A shampoo composition that increases the deposition and retention of benefit agent containing polyacrylate microcapsules onto hair during the cleansing process. The shampoo composition is based on the combination of anionic charged polyacrylate microcapsules, cationic deposition polymers, detersive surfactant, and a carrier.

19 Claims, No Drawings

(56) References Cited

U.S. PATENT DOCUMENTS

| | | |
|---|---|---|
| 4,251,386 A | 2/1981 | Saeki et al. |
| 4,275,055 A | 6/1981 | Nachtigal et al. |
| 4,285,720 A | 8/1981 | Scher |
| 4,323,683 A | 4/1982 | Bolich, Jr. et al. |
| 4,345,080 A | 8/1982 | Bolich, Jr. |
| 4,356,109 A | 10/1982 | Saeki et al. |
| 4,364,837 A | 12/1982 | Pader |
| 4,379,753 A | 4/1983 | Bolich, Jr. |
| 4,381,919 A | 5/1983 | Jacquet et al. |
| 4,422,853 A | 12/1983 | Jacquet et al. |
| 4,423,099 A | 12/1983 | Mueller et al. |
| 4,428,869 A | 1/1984 | Munteanu et al. |
| 4,430,243 A | 2/1984 | Bragg |
| 4,444,699 A | 4/1984 | Hayford |
| 4,446,032 A | 5/1984 | Munteanu et al. |
| 4,450,123 A | 5/1984 | Egawa et al. |
| 4,470,982 A | 9/1984 | Winkler |
| 4,507,280 A | 3/1985 | Pohl et al. |
| 4,515,705 A | 5/1985 | Moeddel |
| 4,529,586 A | 7/1985 | De Marco et al. |
| 4,537,706 A | 8/1985 | Severson, Jr. |
| 4,537,707 A | 8/1985 | Severson, Jr. |
| 4,547,429 A | 10/1985 | Greiner et al. |
| 4,550,862 A | 11/1985 | Barker et al. |
| 4,552,811 A | 11/1985 | Brown et al. |
| 4,561,997 A | 12/1985 | Roehl |
| 4,561,998 A | 12/1985 | Wertz et al. |
| 4,574,110 A | 3/1986 | Asano et al. |
| 4,588,639 A | 5/1986 | Ozono |
| 4,597,898 A | 7/1986 | Vander Meer |
| 4,601,863 A | 7/1986 | Shioi et al. |
| 4,608,250 A | 8/1986 | Jacquet et al. |
| 4,610,927 A | 9/1986 | Igarashi et al. |
| 4,622,267 A | 11/1986 | Riecke |
| 4,663,158 A | 5/1987 | Wolfram et al. |
| 4,708,924 A | 11/1987 | Nagai et al. |
| 4,719,099 A | 1/1988 | Grollier et al. |
| 4,722,865 A | 2/1988 | Huizer |
| 4,741,855 A | 5/1988 | Grote et al. |
| 4,746,467 A | 5/1988 | Sakamoto et al. |
| 4,775,656 A | 10/1988 | Harada et al. |
| 4,780,370 A | 10/1988 | Pointier |
| 4,798,691 A | 1/1989 | Kasai et al. |
| 4,803,947 A | 2/1989 | Ueki et al. |
| 4,824,707 A | 4/1989 | Spector |
| 4,863,626 A | 9/1989 | Coyne et al. |
| 4,865,759 A | 9/1989 | Coyne et al. |
| 4,882,220 A | 11/1989 | Ono et al. |
| 4,908,271 A | 3/1990 | Kasai et al. |
| 4,911,851 A | 3/1990 | Ladd, Jr. et al. |
| 4,917,920 A | 4/1990 | Ono et al. |
| 4,919,841 A | 4/1990 | Kamel et al. |
| 4,957,666 A | 9/1990 | Kawamura et al. |
| 4,968,451 A | 11/1990 | Scheibel et al. |
| 4,972,000 A | 11/1990 | Kawashima et al. |
| 5,009,880 A | 4/1991 | Grollier et al. |
| 5,061,410 A | 10/1991 | Sakamoto et al. |
| 5,066,419 A | 11/1991 | Walley et al. |
| 5,071,706 A | 12/1991 | Soper |
| 5,104,646 A | 4/1992 | Bolich, Jr. et al. |
| 5,105,823 A | 4/1992 | Blum |
| 5,106,609 A | 4/1992 | Bolich, Jr. et al. |
| 5,113,585 A | 5/1992 | Rogers et al. |
| 5,118,756 A | 6/1992 | Asano et al. |
| 5,120,349 A | 6/1992 | Stewart et al. |
| 5,137,646 A | 8/1992 | Schmidt et al. |
| 5,145,675 A | 9/1992 | Won |
| 5,176,903 A | 1/1993 | Goldberg et al. |
| 5,185,155 A | 2/1993 | Behan et al. |
| 5,188,753 A | 2/1993 | Schmidt et al. |
| 5,225,278 A | 7/1993 | Kielbania, Jr. et al. |
| 5,232,613 A | 8/1993 | Bacon et al. |
| 5,232,769 A | 8/1993 | Yamato et al. |
| 5,234,611 A | 8/1993 | Trinh et al. |
| 5,234,682 A | 8/1993 | Macchio et al. |
| 5,277,979 A | 1/1994 | Kielbania, Jr. et al. |
| 5,278,106 A | 1/1994 | Nakashima et al. |
| 5,292,835 A | 3/1994 | Jahns et al. |
| RE34,584 E | 4/1994 | Grote et al. |
| 5,324,444 A | 6/1994 | Berry et al. |
| 5,342,556 A | 8/1994 | Traubel et al. |
| 5,362,565 A | 11/1994 | Murano et al. |
| 5,366,652 A | 11/1994 | Capeci et al. |
| 5,370,881 A | 12/1994 | Fuisz |
| 5,380,756 A | 1/1995 | Andrews et al. |
| 5,407,609 A | 4/1995 | Tice et al. |
| 5,468,473 A | 11/1995 | Mullen |
| 5,486,303 A | 1/1996 | Capeci et al. |
| 5,487,884 A | 1/1996 | Bissett et al. |
| 5,489,392 A | 2/1996 | Capeci et al. |
| 5,516,448 A | 5/1996 | Capeci et al. |
| 5,565,145 A | 10/1996 | Watson et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,580,578 A | 12/1996 | Oshlack et al. |
| 5,595,967 A | 1/1997 | Miracle et al. |
| 5,596,051 A | 1/1997 | Jahns et al. |
| 5,597,936 A | 1/1997 | Perkins et al. |
| 5,607,980 A | 3/1997 | McAtee et al. |
| 5,611,972 A | 3/1997 | Tararuj et al. |
| 5,637,401 A | 6/1997 | Berman et al. |
| 5,648,328 A | 7/1997 | Angell et al. |
| 5,652,228 A | 7/1997 | Bissett |
| 5,656,584 A | 8/1997 | Angell et al. |
| 5,674,478 A | 10/1997 | Dodd et al. |
| 5,681,852 A | 10/1997 | Bissett |
| 5,691,297 A | 11/1997 | Nassano et al. |
| 5,702,714 A | 12/1997 | Goss |
| 5,716,938 A | 2/1998 | Provitt |
| 5,723,420 A | 3/1998 | Wei et al. |
| 5,725,869 A | 3/1998 | Lo |
| 5,750,122 A | 5/1998 | Evans et al. |
| 5,756,436 A | 5/1998 | Royce et al. |
| 5,759,573 A | 6/1998 | Kim |
| 5,782,409 A | 7/1998 | Paul |
| 5,783,536 A | 7/1998 | Farrell et al. |
| 5,800,805 A | 9/1998 | Salas |
| 5,807,956 A | 9/1998 | Czech |
| 5,827,538 A | 10/1998 | Cussler et al. |
| 5,833,971 A | 11/1998 | Baldwin |
| 5,856,409 A | 1/1999 | Ziemelis et al. |
| 5,876,755 A | 3/1999 | Perring et al. |
| 5,879,584 A | 3/1999 | Bianchetti et al. |
| 5,885,701 A | 3/1999 | Berman et al. |
| 5,929,022 A | 7/1999 | Velazquez |
| 5,945,085 A | 8/1999 | Salas et al. |
| 5,962,018 A | 10/1999 | Curtis et al. |
| 5,972,859 A | 10/1999 | Farrell et al. |
| 5,981,681 A | 11/1999 | Czech |
| 6,024,943 A | 2/2000 | Ness et al. |
| 6,075,003 A | 6/2000 | Haq et al. |
| 6,159,485 A | 12/2000 | Yu et al. |
| 6,182,365 B1 | 2/2001 | Tseng et al. |
| 6,185,822 B1 | 2/2001 | Tseng et al. |
| 6,194,375 B1 | 2/2001 | Ness et al. |
| 6,207,782 B1 | 3/2001 | Czech et al. |
| 6,221,326 B1 | 4/2001 | Amiche |
| 6,221,826 B1 | 4/2001 | Surutzidis et al. |
| 6,225,464 B1 | 5/2001 | Hiler, II et al. |
| 6,228,398 B1 | 5/2001 | Devane et al. |
| 6,235,274 B1 | 5/2001 | Lou et al. |
| 6,235,773 B1 | 5/2001 | Bissett |
| 6,245,366 B1 | 6/2001 | Popplewell et al. |
| 6,245,733 B1 | 6/2001 | Mosbaugh |
| 6,248,364 B1 | 6/2001 | Sengupta et al. |
| 6,258,857 B1 | 7/2001 | Iijima et al. |
| 6,294,514 B1 | 9/2001 | Welling |
| 6,298,558 B1 | 10/2001 | Tseng et al. |
| 6,306,812 B1 | 10/2001 | Perkins et al. |
| 6,325,995 B1 | 12/2001 | El-Nokaly et al. |
| 6,326,348 B1 | 12/2001 | Vinson et al. |
| 6,329,057 B1 | 12/2001 | Dungworth et al. |

(56) References Cited

U.S. PATENT DOCUMENTS

| | | |
|---|---|---|
| 6,348,218 B1 | 2/2002 | Hed et al. |
| 6,362,159 B1 | 3/2002 | Aguadisch et al. |
| 6,368,633 B1 | 4/2002 | Lou et al. |
| 6,375,872 B1 | 4/2002 | Chao |
| 6,375,983 B1 | 4/2002 | Kantor et al. |
| 6,399,192 B1 | 6/2002 | Pinna et al. |
| 6,428,796 B1 | 8/2002 | Gers-Barlag et al. |
| 6,451,754 B1 | 9/2002 | Rowland et al. |
| 6,482,969 B1 | 11/2002 | Helmrick et al. |
| 6,489,047 B2 | 12/2002 | Mosbaugh |
| 6,498,135 B1 | 12/2002 | Angell et al. |
| 6,503,495 B1 | 1/2003 | Alwattari et al. |
| 6,531,156 B1 | 3/2003 | Clark et al. |
| 6,558,706 B2 | 5/2003 | Kantor et al. |
| 6,592,990 B2 | 7/2003 | Schwantes |
| 6,594,904 B1 | 7/2003 | Tseng |
| 6,607,717 B1 | 8/2003 | Johnson et al. |
| 6,608,017 B1 | 8/2003 | Dihora et al. |
| 6,638,591 B2 | 10/2003 | Bowen et al. |
| 6,670,311 B1 | 12/2003 | Aldcroft et al. |
| 6,682,749 B1 | 1/2004 | Potechin et al. |
| 6,696,049 B2 | 2/2004 | Vatter et al. |
| 6,696,400 B2 | 2/2004 | Puelle Andrade et al. |
| 6,703,032 B2 | 3/2004 | Gers-Barlag et al. |
| 6,730,325 B2 | 5/2004 | Devane et al. |
| 6,733,790 B1 | 5/2004 | Garces Garces |
| 6,767,880 B1 | 7/2004 | Foley et al. |
| 6,769,271 B2 | 8/2004 | Mosbaugh |
| 6,770,293 B2 | 8/2004 | Angel et al. |
| 6,780,507 B2 | 8/2004 | Toreki et al. |
| 6,783,770 B2 | 8/2004 | Angel et al. |
| 6,790,814 B1 | 9/2004 | Marin et al. |
| 6,793,936 B2 | 9/2004 | Devane et al. |
| 6,797,683 B2 | 9/2004 | Shana'a et al. |
| 6,800,598 B1 | 10/2004 | Waeschenbach et al. |
| 6,806,249 B2 | 10/2004 | Yang et al. |
| 6,846,785 B2 | 1/2005 | Patel |
| 6,849,584 B2 * | 2/2005 | Geary et al. ................ 510/119 |
| 6,849,591 B1 | 2/2005 | Boeckh et al. |
| 6,864,223 B2 | 3/2005 | Smith et al. |
| 6,869,923 B1 | 3/2005 | Cunningham et al. |
| 6,872,853 B1 | 3/2005 | Van Der Schaaf et al. |
| 6,881,482 B2 | 4/2005 | Vasisht |
| 6,902,742 B2 | 6/2005 | Devane et al. |
| 6,916,481 B1 | 7/2005 | Prud'Homme et al. |
| 6,939,992 B2 | 9/2005 | Van Der Schaaf et al. |
| 6,944,952 B1 | 9/2005 | Tseng |
| 6,951,836 B2 | 10/2005 | Jahns et al. |
| 6,955,823 B2 | 10/2005 | Casson et al. |
| 6,958,313 B2 | 10/2005 | Caswell et al. |
| 6,982,256 B2 | 1/2006 | Votteler et al. |
| 7,015,186 B2 | 3/2006 | Aussant et al. |
| 7,041,767 B2 | 5/2006 | Lange et al. |
| 7,053,034 B2 | 5/2006 | Shefer et al. |
| 7,069,658 B2 | 7/2006 | Tseng |
| 7,105,064 B2 | 9/2006 | Popplewell et al. |
| 7,119,057 B2 | 10/2006 | Popplewell et al. |
| 7,122,512 B2 | 10/2006 | Brain et al. |
| 7,125,835 B2 | 10/2006 | Bennett et al. |
| 7,137,570 B2 | 11/2006 | Wheatley et al. |
| 7,159,792 B2 | 1/2007 | Wheatley et al. |
| 7,186,679 B2 | 3/2007 | Shepherd, Jr. |
| 7,186,680 B2 | 3/2007 | Caswell et al. |
| 7,192,599 B2 | 3/2007 | Mercier et al. |
| 7,196,049 B2 | 3/2007 | Brain et al. |
| 7,204,998 B2 | 4/2007 | Holzner et al. |
| 7,208,463 B2 | 4/2007 | Heltovics et al. |
| 7,208,465 B2 | 4/2007 | Heltovics et al. |
| 7,211,273 B2 | 5/2007 | Hsu |
| 7,211,556 B2 | 5/2007 | Heibel et |
| 7,217,777 B2 | 5/2007 | Lange et al. |
| 7,226,607 B2 | 6/2007 | Uchiyama et al. |
| 7,229,611 B2 | 6/2007 | Zamudio-Tena et al. |
| 7,235,261 B2 | 6/2007 | Smith et al. |
| 7,241,835 B2 | 7/2007 | O'Brien et al. |
| 7,247,374 B2 | 7/2007 | Haggquist |
| 7,270,828 B2 | 9/2007 | Masuda et al. |
| 7,279,542 B2 | 10/2007 | Ouali et al. |
| 7,293,719 B2 | 11/2007 | Wheatley et al. |
| 7,294,612 B2 | 11/2007 | Popplewell et al. |
| 7,311,900 B2 | 12/2007 | Conover |
| 7,338,928 B2 | 3/2008 | Lau et al. |
| 7,375,875 B2 | 5/2008 | Whitesides et al. |
| 7,381,417 B2 | 6/2008 | Gamez-Garcia |
| 7,399,324 B2 | 7/2008 | Roddenbery et al. |
| 7,407,650 B2 | 8/2008 | Heltovics et al. |
| 7,413,731 B2 | 8/2008 | Heltovics et al. |
| 7,442,838 B2 | 10/2008 | Van Der Schaaf et al. |
| 7,452,547 B2 | 11/2008 | Lambino et al. |
| 7,465,439 B2 | 12/2008 | Avery et al. |
| 7,491,687 B2 | 2/2009 | Popplewell et al. |
| 7,521,124 B2 | 4/2009 | Ahn et al. |
| 7,524,807 B2 | 4/2009 | Clapp et al. |
| 7,532,388 B2 | 5/2009 | Whitesides et al. |
| 7,538,077 B2 | 5/2009 | Sichmann et al. |
| 7,538,078 B2 | 5/2009 | Holzner et al. |
| 7,569,528 B2 | 8/2009 | Lant et al. |
| 7,575,633 B2 | 8/2009 | Romanin |
| 7,575,804 B2 | 8/2009 | Lang-Wittkowski et al. |
| 7,585,824 B2 | 9/2009 | Popplewell et al. |
| 7,585,825 B2 | 9/2009 | Artiga Gonzalez et al. |
| 7,585,832 B2 | 9/2009 | Smith et al. |
| 7,736,695 B2 | 6/2010 | Schwantes et al. |
| 7,794,836 B2 | 9/2010 | Vasishtha et al. |
| 7,799,421 B2 | 9/2010 | Goodson et al. |
| 7,799,752 B2 | 9/2010 | Ness et al. |
| 7,803,422 B2 | 9/2010 | Schwantes et al. |
| 7,833,960 B2 | 11/2010 | Lei et al. |
| 7,871,588 B2 | 1/2011 | Lindner et al. |
| 7,985,445 B2 | 7/2011 | Schwantes et al. |
| 8,022,029 B2 | 9/2011 | Broze et al. |
| 8,026,205 B2 | 9/2011 | Broze et al. |
| 8,053,405 B2 | 11/2011 | Narayanan et al. |
| 8,067,089 B2 | 11/2011 | Schwantes |
| 8,071,214 B2 | 12/2011 | Schwantes |
| 8,093,201 B2 | 1/2012 | Broze et al. |
| 8,110,284 B2 | 2/2012 | Naigertsik et al. |
| 8,119,163 B2 | 2/2012 | Devane et al. |
| 8,129,327 B2 | 3/2012 | Zhang et al. |
| 8,147,808 B2 | 4/2012 | Scavone et al. |
| 8,158,571 B2 | 4/2012 | Alonso et al. |
| 8,163,207 B2 | 4/2012 | Jung et al. |
| 8,192,838 B2 | 6/2012 | Goodson et al. |
| 8,206,820 B2 | 6/2012 | Bogaerts et al. |
| 8,246,869 B2 | 8/2012 | Stowell |
| 8,252,356 B2 | 8/2012 | Ogura et al. |
| 8,304,075 B2 | 11/2012 | Lang-Wittkowski et al. |
| 8,329,154 B2 | 12/2012 | Uchiyama et al. |
| 8,349,300 B2 | 1/2013 | Wells et al. |
| 8,354,369 B2 | 1/2013 | Beaussoubre et al. |
| 8,426,194 B2 | 4/2013 | Cao et al. |
| 8,460,791 B2 | 6/2013 | Hentze et al. |
| 8,460,864 B2 | 6/2013 | Cao et al. |
| 8,470,762 B2 | 6/2013 | Broze et al. |
| 2002/0016269 A1 | 2/2002 | Noda et al. |
| 2002/0102286 A1 | 8/2002 | Kantor et al. |
| 2002/0136773 A1 | 9/2002 | Scher et al. |
| 2002/0169233 A1 | 11/2002 | Schwantes |
| 2003/0017126 A1 | 1/2003 | Mahadeshwar et al. |
| 2003/0017959 A1 | 1/2003 | Baeck et al. |
| 2003/0024997 A1 | 2/2003 | Welch et al. |
| 2003/0031722 A1 | 2/2003 | Cao et al. |
| 2003/0077378 A1 | 4/2003 | Lou et al. |
| 2003/0108501 A1 | 6/2003 | Hofrichter et al. |
| 2003/0109391 A1 | 6/2003 | Midha et al. |
| 2003/0125222 A1 | 7/2003 | Jahns et al. |
| 2003/0139312 A1 | 7/2003 | Caswell et al. |
| 2003/0152542 A1 | 8/2003 | Decoster et al. |
| 2003/0170304 A1 | 9/2003 | Devane et al. |
| 2003/0194416 A1 | 10/2003 | Shefer et al. |
| 2003/0199412 A1 | 10/2003 | Gupta et al. |
| 2003/0203978 A1 | 10/2003 | O'Brien et al. |
| 2003/0215417 A1 | 11/2003 | Uchiyama et al. |
| 2003/0216488 A1 | 11/2003 | Uchiyama et al. |

(56) References Cited

U.S. PATENT DOCUMENTS

| | | |
|---|---|---|
| 2003/0220220 A1 | 11/2003 | Bach et al. |
| 2004/0043078 A1 | 3/2004 | Herault |
| 2004/0071742 A1 | 4/2004 | Popplewell et al. |
| 2004/0091445 A1 | 5/2004 | Dykstra et al. |
| 2004/0101577 A1 | 5/2004 | Ahn et al. |
| 2004/0109920 A1 | 6/2004 | Reuscher et al. |
| 2004/0110898 A1 | 6/2004 | Dreja et al. |
| 2004/0137028 A1 | 7/2004 | de la Poterie |
| 2004/0138088 A1 | 7/2004 | Pereira et al. |
| 2004/0175347 A1 | 9/2004 | Bissett |
| 2004/0175404 A1 | 9/2004 | Shefer et al. |
| 2004/0197405 A1 | 10/2004 | Devane et al. |
| 2004/0208902 A1 | 10/2004 | Gupta |
| 2004/0214742 A1 | 10/2004 | Meli et al. |
| 2004/0220062 A1 | 11/2004 | Pereira et al. |
| 2004/0229769 A1 | 11/2004 | Smith et al. |
| 2005/0014674 A1 | 1/2005 | Liechty et al. |
| 2005/0038188 A1 | 2/2005 | Ahn et al. |
| 2005/0043209 A1 | 2/2005 | Schmiedel et al. |
| 2005/0048549 A1 | 3/2005 | Cao et al. |
| 2005/0112152 A1* | 5/2005 | Popplewell et al. .......... 424/401 |
| 2005/0113282 A1 | 5/2005 | Parekh et al. |
| 2005/0119351 A1 | 6/2005 | Van Der Schaaf et al. |
| 2005/0129759 A1 | 6/2005 | Sojka |
| 2005/0169793 A1 | 8/2005 | Wheatley et al. |
| 2005/0226900 A1 | 10/2005 | Winton Brooks et al. |
| 2005/0227907 A1 | 10/2005 | Lee et al. |
| 2005/0276831 A1 | 12/2005 | Dihora et al. |
| 2006/0008646 A1 | 1/2006 | Haggquist |
| 2006/0099168 A1 | 5/2006 | Corzani et al. |
| 2006/0116304 A1 | 6/2006 | McRitchie et al. |
| 2006/0127430 A1 | 6/2006 | Gupta |
| 2006/0134154 A1 | 6/2006 | Giles et al. |
| 2006/0160711 A1 | 7/2006 | Frank |
| 2006/0165740 A1 | 7/2006 | Frank |
| 2006/0166855 A1 | 7/2006 | Murad |
| 2006/0240105 A1 | 10/2006 | Devane et al. |
| 2006/0248665 A1 | 11/2006 | Pluyter et al. |
| 2006/0258557 A1 | 11/2006 | Popplewell et al. |
| 2006/0263311 A1 | 11/2006 | Scavone et al. |
| 2006/0263312 A1 | 11/2006 | Scavone et al. |
| 2006/0263313 A1 | 11/2006 | Scavone et al. |
| 2006/0263518 A1 | 11/2006 | Schwantes et al. |
| 2006/0263519 A1* | 11/2006 | Schwantes et al. ........ 427/213.3 |
| 2006/0263898 A1 | 11/2006 | Paget et al. |
| 2006/0275237 A1 | 12/2006 | Bissett et al. |
| 2006/0292098 A1 | 12/2006 | Scavone et al. |
| 2007/0020205 A1 | 1/2007 | Blin et al. |
| 2007/0031463 A1 | 2/2007 | Fotinos et al. |
| 2007/0041929 A1 | 2/2007 | Torgerson et al. |
| 2007/0048339 A1 | 3/2007 | Popplewell et al. |
| 2007/0071781 A1 | 3/2007 | Louys, Jr. et al. |
| 2007/0071978 A1 | 3/2007 | Sojka et al. |
| 2007/0078071 A1 | 4/2007 | Lee et al. |
| 2007/0122481 A1 | 5/2007 | Liversidge et al. |
| 2007/0123442 A1 | 5/2007 | Holzner et al. |
| 2007/0134411 A1 | 6/2007 | Cont et al. |
| 2007/0138671 A1 | 6/2007 | Anastasiou et al. |
| 2007/0138672 A1 | 6/2007 | Lee et al. |
| 2007/0138673 A1 | 6/2007 | Lee et al. |
| 2007/0138674 A1 | 6/2007 | Anastasiou et al. |
| 2007/0160561 A1 | 7/2007 | Ouali et al. |
| 2007/0160675 A1 | 7/2007 | Devane et al. |
| 2007/0173433 A1 | 7/2007 | Heibel et al. |
| 2007/0202063 A1 | 8/2007 | Dihora et al. |
| 2007/0207109 A1 | 9/2007 | Peffly et al. |
| 2007/0207174 A1 | 9/2007 | Pluyter et al. |
| 2007/0224274 A1 | 9/2007 | Siol |
| 2007/0248553 A1 | 10/2007 | Scavone et al. |
| 2007/0286837 A1 | 12/2007 | Torgerson et al. |
| 2007/0286904 A1 | 12/2007 | Popplewell et al. |
| 2007/0292361 A1 | 12/2007 | Virgallito et al. |
| 2007/0298061 A1 | 12/2007 | Boghani et al. |
| 2008/0008750 A1 | 1/2008 | Tochio et al. |
| 2008/0040082 A1 | 2/2008 | Stanton et al. |
| 2008/0057021 A1 | 3/2008 | Dykstra et al. |
| 2008/0102121 A1 | 5/2008 | Devane et al. |
| 2008/0107615 A1 | 5/2008 | Keene et al. |
| 2008/0113025 A1 | 5/2008 | Devane et al. |
| 2008/0118556 A1 | 5/2008 | Devane et al. |
| 2008/0128941 A1 | 6/2008 | Lopez et al. |
| 2008/0187596 A1 | 8/2008 | Dihora et al. |
| 2008/0199503 A1 | 8/2008 | Camargo et al. |
| 2008/0200359 A1 | 8/2008 | Smets et al. |
| 2008/0200363 A1 | 8/2008 | Smets et al. |
| 2008/0213451 A1 | 9/2008 | Ogura et al. |
| 2008/0226684 A1 | 9/2008 | Peppas |
| 2008/0311064 A1 | 12/2008 | Lei et al. |
| 2008/0317788 A1 | 12/2008 | Louzan Garcia et al. |
| 2009/0022764 A1 | 1/2009 | Frater et al. |
| 2009/0029900 A1 | 1/2009 | Cetti et al. |
| 2009/0035365 A1 | 2/2009 | Popplewell et al. |
| 2009/0047434 A1 | 2/2009 | Trophardy |
| 2009/0053165 A1* | 2/2009 | Brown et al. .............. 424/78.08 |
| 2009/0081265 A1 | 3/2009 | Peppas |
| 2009/0118399 A1 | 5/2009 | Benbakoura et al. |
| 2009/0149479 A1 | 6/2009 | Jenkins et al. |
| 2009/0202465 A1 | 8/2009 | Mougin et al. |
| 2009/0209661 A1 | 8/2009 | Somerville Roberts et al. |
| 2009/0221463 A1 | 9/2009 | Kitko et al. |
| 2009/0232857 A1 | 9/2009 | Peppas |
| 2009/0232858 A1 | 9/2009 | Peppas et al. |
| 2009/0247449 A1 | 10/2009 | Burdis et al. |
| 2009/0252789 A1 | 10/2009 | Trophardy |
| 2009/0258042 A1 | 10/2009 | Anastasiou et al. |
| 2009/0274905 A1 | 11/2009 | Schwantes |
| 2009/0275494 A1 | 11/2009 | Ferguson et al. |
| 2009/0289216 A1 | 11/2009 | Jung et al. |
| 2009/0324660 A1 | 12/2009 | Cetti et al. |
| 2010/0003518 A1 | 1/2010 | Grey |
| 2010/0061954 A1 | 3/2010 | Adams et al. |
| 2010/0068163 A1 | 3/2010 | Lu |
| 2010/0104611 A1 | 4/2010 | Chan et al. |
| 2010/0104612 A1 | 4/2010 | Cropper et al. |
| 2010/0104613 A1 | 4/2010 | Chan et al. |
| 2010/0119679 A1 | 5/2010 | Dihora et al. |
| 2010/0216684 A1 | 8/2010 | Ferguson et al. |
| 2010/0275384 A1 | 11/2010 | Broze et al. |
| 2010/0286018 A1 | 11/2010 | Hentze et al. |
| 2011/0003152 A1 | 1/2011 | Grey |
| 2011/0008427 A1 | 1/2011 | Biggs et al. |
| 2011/0008435 A1 | 1/2011 | Devane et al. |
| 2011/0020416 A1 | 1/2011 | Pluyter et al. |
| 2011/0033513 A1 | 2/2011 | Lei et al. |
| 2011/0093246 A1 | 4/2011 | Stanton et al. |
| 2011/0267702 A1 | 11/2011 | Fujimoto et al. |
| 2011/0268778 A1 | 11/2011 | Dihora et al. |
| 2011/0268802 A1 | 11/2011 | Dihora et al. |
| 2011/0269657 A1 | 11/2011 | Dihora et al. |
| 2011/0269658 A1 | 11/2011 | Dihora et al. |
| 2012/0010120 A1 | 1/2012 | Somerville Roberts et al. |
| 2012/0076839 A1 | 3/2012 | Chan et al. |
| 2012/0121677 A1 | 5/2012 | Franklin |
| 2012/0177924 A1 | 7/2012 | Jung et al. |
| 2012/0276175 A1 | 11/2012 | Dihora et al. |
| 2012/0276210 A1 | 11/2012 | Dihora et al. |
| 2012/0282309 A1 | 11/2012 | Dihora et al. |
| 2012/0322709 A1 | 12/2012 | Li et al. |
| 2013/0137625 A1 | 5/2013 | Stowell |

FOREIGN PATENT DOCUMENTS

| | | |
|---|---|---|
| DE | 10062585 A1 | 6/2002 |
| DE | 102005029777 | 1/2007 |
| DE | 102006058253 | 6/2008 |
| DE | 102008044700 | 2/2010 |
| EP | 0303461 A1 | 2/1989 |
| EP | 0462709 A2 | 12/1991 |
| EP | 0510761 A1 | 10/1992 |
| EP | 0523287 A1 | 1/1993 |
| EP | 0290223 B1 | 12/1994 |
| EP | 0820762 A1 | 1/1998 |
| EP | 0829259 A1 | 3/1998 |
| EP | 0535942 B1 | 2/1999 |

(56) References Cited

FOREIGN PATENT DOCUMENTS

| | | |
|---|---|---|
| EP | 1034705 | 9/2000 |
| EP | 1201743 A1 | 5/2002 |
| EP | 1243318 | 9/2002 |
| EP | 1243320 | 9/2002 |
| EP | 1247568 | 10/2002 |
| EP | 1024785 B1 | 1/2003 |
| EP | 1030734 B1 | 8/2003 |
| EP | 1023041 B1 | 1/2005 |
| EP | 1502646 A1 | 2/2005 |
| EP | 1637188 | 3/2006 |
| EP | 1702674 | 9/2006 |
| EP | 1850887 | 11/2007 |
| EP | 1600151 B1 | 8/2008 |
| EP | 2090284 | 8/2009 |
| EP | 2132294 | 12/2009 |
| FR | 2702961 | 9/1994 |
| FR | 2881048 | 7/2006 |
| GB | 1451411 | 10/1976 |
| GB | 1478788 | 7/1977 |
| GB | 1546480 | 5/1979 |
| GB | 2062570 | 5/1981 |
| GB | 2217603 A | 1/1989 |
| GB | 2334724 A | 1/1999 |
| JP | 54-5051 | 1/1979 |
| JP | 58-19261 | 2/1983 |
| JP | 59-139268 | 8/1984 |
| JP | 61-244366 | 10/1986 |
| JP | 62116506 | 5/1987 |
| JP | 01-256965 | 10/1989 |
| JP | 02-036803 | 2/1990 |
| JP | 02-052661 | 2/1990 |
| JP | 04-021513 | 1/1992 |
| JP | 04-082558 | 3/1992 |
| JP | 04-156851 | 5/1992 |
| JP | 05-017338 | 1/1993 |
| JP | 06-000361 | 1/1994 |
| JP | 06-041576 U | 6/1994 |
| JP | 07-075666 | 3/1995 |
| JP | 07-305049 | 11/1995 |
| JP | 10195478 A | 7/1998 |
| JP | 10231119 | 9/1998 |
| JP | 2001049287 | 2/2001 |
| JP | 2002326904 | 11/2002 |
| JP | 2003099986 A | 4/2003 |
| JP | 2003161893 | 6/2003 |
| JP | 2004099743 | 4/2004 |
| JP | 2005194308 | 7/2005 |
| JP | 2008156565 | 7/2008 |
| JP | 2009035454 | 2/2009 |
| JP | 2009290236 | 12/2009 |
| KR | 20090082704 | 9/2010 |
| WO | 84/03630 A1 | 9/1984 |
| WO | 92/20771 | 11/1992 |
| WO | 93/08600 A1 | 4/1993 |
| WO | 97/47720 A2 | 12/1997 |
| WO | 98/12298 A2 | 3/1998 |
| WO | 98/26808 A2 | 6/1998 |
| WO | 00/32601 | 6/2000 |
| WO | 00/41528 | 7/2000 |
| WO | 00-65020 | 11/2000 |
| WO | 00/67718 A1 | 11/2000 |
| WO | 01/41915 | 6/2001 |
| WO | 01/41915 A1 | 6/2001 |
| WO | 01/74310 A2 | 10/2001 |
| WO | 03/002248 A1 | 1/2003 |
| WO | 03/020867 A1 | 3/2003 |
| WO | 2004/006967 A1 | 1/2004 |
| WO | 2004/060418 A1 | 7/2004 |
| WO | 2004/096895 A1 | 11/2004 |
| WO | 2005/041908 A1 | 5/2005 |
| WO | 2005/047232 A1 | 5/2005 |
| WO | 2005/055990 A1 | 6/2005 |
| WO | 2006/027664 A2 | 3/2006 |
| WO | 2006/127454 | 11/2006 |
| WO | 2007/040517 | 4/2007 |
| WO | 2007/128326 A1 | 11/2007 |
| WO | 2007/137441 A1 | 12/2007 |
| WO | 2008/005693 A2 | 1/2008 |
| WO | 2008/058868 | 5/2008 |
| WO | 2008/129028 A1 | 10/2008 |
| WO | 2008/145874 A1 | 12/2008 |
| WO | 2009/047127 A1 | 4/2009 |
| WO | 2009/047745 A2 | 4/2009 |
| WO | 2009/080695 A1 | 7/2009 |
| WO | 2009/083941 A2 | 7/2009 |
| WO | 2009/093812 A1 | 7/2009 |
| WO | 2009/106318 A2 | 9/2009 |
| WO | 2009/134234 A1 | 11/2009 |
| WO | 2010/079466 A2 | 7/2010 |

OTHER PUBLICATIONS

PCT International Search Report and Written Opinion dated Nov. 27, 2012, PCT/US2012/032101.
PCT International Search Report and Written Opinion dated Nov. 27, 2012, PCT/US2012/032065.
International Search Report for PCT/US2005/020223, mailed May 10, 2005, 4 pages.
International Search Report for PCT/IB2010/052127, mailed May 12, 2011, 5 pages.
International Search Report for PCT/IB2010/052128, mailed Dec. 28, 2010, 3 pages.
International Search Report for PCT/IB2010/052121 mailed Feb. 16, 2011, 3 pages.
International Search Report for PCT/IB2010/052120 mailed Dec. 29, 2010, 4 pages.
Huber et al.—"Capsular Adhesives", TAPPI, vol. 49, No. 5, pp. 41A-44A, May 1966.
Leo, Albert J., et al.—Methods of Calculating Partition Coefficients, Comprehensive Medicinal Chemistry, vol. 4, p. 295, 1990.
Zhang, Z., et al.—"Mechanical Properties of Melamine-Formaldehyde Microcapsules", J. Microencapsulation, vol. 18, No. 5, pp. 593-602, 2001.
Brunauer, et al.—"Absorption of Gases in Multimolecular Layers"—Journal of the American Chemical Society, vol. 60, pp. 309-319, 1938.
Washburn, E.W.—"The Dynamics of Capillary Flow"—Phys. Rev., 17 374-375, 1921.
Fowkes, F.M.—"Attractive Forces at Interfaces"—Industrial and Engineering Chemistry, vol. 56, No. 12, pp. 40-52, 1964.
Good, R.J., et al.—A Theory for Estimation of Surface and Interfacial Energies, III, Estimation of Surface Energies or Solids from Contact Angle Data, L.A.; Journal of Phys. Chem., vol. 64, pp. 561-565, 1960.

* cited by examiner

SHAMPOO COMPOSITIONS WITH INCREASED DEPOSITION OF POLYACRYLATE MICROCAPSULES

CROSS REFERENCE TO RELATED APPLICATION

This application claims the benefit of U.S. Provisional Application Ser. No. 61/472,898 filed Apr. 7, 2011.

FIELD OF THE INVENTION

The present invention relates to shampoo compositions containing polyacrylate microcapsules, wherein the polyacrylate microcapsules have increased deposition onto hair.

BACKGROUND OF THE INVENTION

Many of the shampoo products in the market today work to deliver benefits to hair by depositing benefit agents such as perfumes, silicones, dyes, and anti-dandruff agents onto the hair during washing. As a result, there is a desire to maximize the effectiveness of such benefit agents by increasing their delivery and retention onto hair. One method of achieving this objective is to encapsulate such benefit agents in microcapsules. While these microcapsules are able to encapsulate a wide variety of benefit agents and deliver them to hair, they are still often washed off of the hair before their benefit can be fully realized. Consumers today desire shampoo compositions that deposit and retain encapsulated benefit agents on the hair and the scalp, even after the rinsing process is complete.

However, obtaining good deposition of microcapsules onto hair during cleansing is further complicated by the action of detersive surfactants in shampoo. Detersive surfactants are designed to carry away oil, grease, and dirt from the hair and scalp, but can also interfere with the deposition of the encapsulated benefit agents. When microcapsules are washed away, relatively high levels of encapsulated benefit agents may be needed in the shampoo composition to deliver the consumer desired benefit.

Accordingly, there is a need for a shampoo composition that provides an increased deposition of encapsulated benefit agents onto the hair. In addition, there is a need for a polymer system that associates with microcapsule surfaces, and that when sheared, allows the encapsulated benefit agents to be released. Furthermore, there is a need for a shampoo composition that provides an increased retention of encapsulated benefit agents onto the hair during the rinse-off process.

SUMMARY OF THE INVENTION

A shampoo composition for cleansing a substrate, comprising: from about 0.001% to about 10% of an anionic charged polyacrylate microcapsule; from about 0.01% to about 2% of a cationic deposition polymer; from about 2% to about 25% of a detersive surfactant; and a carrier.

A method of making a shampoo composition, wherein the composition is formed by a process comprising the steps of: coating a polyacrylate microcapsule with an anionic emulsifier to form an anionic polyacrylate microcapsule; combining the anionic polyacrylate microcapsule with a cationic deposition polymer to form a premix; adding the premix to a detersive composition comprising surfactant and a carrier.

A method of making a shampoo composition, wherein the composition is formed by a process comprising the steps of: coating a polyacrylate microcapsule with an anionic emulsifier to form an anionic polyacrylate microcapsule; combining the anionic polyacrylate microcapsule with a cationic deposition polymer to form a premix; adding the premix to an anionic surfactant; adding the resulting composition of step (c) to a detersive composition comprising surfactant and a carrier.

DETAILED DESCRIPTION OF THE INVENTION

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

DEFINITIONS

As used herein, the term "personal care composition" includes, unless otherwise indicated, any personal care composition that can be applied to the keratinaceous surfaces of the body including the skin and/or hair. The personal cleansing compositions can be, for example, formulated as shampoos, hair tonics, hair colorants, sprays, mousses and/or other styling products.

As used herein, the term "fluid" includes liquids and gels.

As used herein, the terms "microcapsule," "encapsulated benefit agents," and "solid particulates," refers to polyacrylate microcapsules.

As used herein, the term "premix" refers to the combination of anionic polyacrylate microcapsules with cationic deposition polymers.

As used herein, the term "shampoo composition" refers to the combination of detersive surfactant and carrier.

As used herein, the articles including "a" and "an" when used in a claim, are understood to mean one or more of what is claimed or described.

As used herein, the terms "include," "includes," and "including," are meant to be non-limiting.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Benefits of Anionic Polyacrylate Microcapsules

Consumers desire a shampoo that deposits and retains encapsulated benefit agents onto their hair and scalp during the cleansing process. Traditionally, a variety of approaches have been employed to improve deposition of microcapsules, including (1) using specific block copolymers to covalently bind to the microcapsules, and (2) using cationic water soluble polymers to coat the microcapsules in order to increase the affinity of the microcapsules to the substrate of interest. However, it is desired to have improved deposition over the traditional approaches.

It has been surprisingly found that a synergy exists between anionic emulsifiers and polyacrylate microcapsules, resulting in anionic polyacrylate microcapsules. When such anionic microcapsules are mixed with certain cationic deposition polymers, microstructures are formed at the surface of the anionic polyacrylate. Such anionic microstructures display high viscoelasticity, remain in tact even upon dilution during cleansing, and display strong adhesion to keratinaceous hair surfaces. Combined with shampoo, these properties result in improved delivery efficiency of the encapsulated benefit agents to hair.

It is believed that the shampoo compositions comprising anionic polyacrylate microcapsules, along with specific cationic deposition polymers, delivers a higher deposition rate than shampoos containing non-anionic polyacrylates. In addition, anionic polyacrylate microcapsules with specific cationic deposition polymers also have a higher retention rate on hair even in the presence of detersive surfactants and carriers found in shampoo compositions. Applicants surprising discovery of adding anionic emulsifier to microcapsules to form anionic microcapsules can be accomplished by either: (1) adding the anionic emulsifier to an already formed microcapsule or (2) allowing the anionic emulsifier to associate with the microcapsule surface during the microcapsule making process. Once formed, the anionic polyacrylate microcapsules are combined with the specific cationic polymer(s) chosen to form a premix for addition to an anionic surfactant containing shampoo composition.

Anionic Emulsifier

The addition of an anionic emulsifier forms a microstructure with a specified cationic deposition polymer at the external surface of the microcapsules, i.e., the anionic emulsifier is at least a part of the external surface of the microcapsules, or is physically or chemically bound to the external surface of the microcapsules. Such physical bindings include, for example, hydrogen bonding, ionic interactions, hydrophobic interactions, and electron transfer interactions. Such chemical bindings include, for example, covalent bindings such as covalent grafting and crosslinking.

The anionic emulsifier is present at a level by weight of from about 0.1% to about 40%, from about 0.5% to about 10%, or from about 0.5% to about 5%, by weight of the polyacrylate microcapsule.

A variety of anionic emulsifiers can be used in the shampoo composition of the present invention as described below. The anionic emulsifiers include, by way of illustrating and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

In addition, it is desirable to use anionic emulsifiers that have acrylate functionality since these can be covalently linked to the shell portion of the polyacrylate microcapsules during the microcapsule making process. Anionic emulsifiers useful herein include, but aren't limited to: poly(meth)acrylic acid; copolymers of (meth)acrylic acids and its (meth)acrylates with C1-22 alkyl, C1-C8 alkyl, butyl; copolymers of (meth)acrylic acids and (meth)acrylamide; Carboxyvinylpolymer; acrylate copolymers such as Acrylate/C10-30 alkyl acrylate crosspolymer, Acrylic acid/vinyl ester copolymer/Acrylates/Vinyl Isodecanoate crosspolymer, Acrylates/Palmeth-25 Acrylate copolymer, Acrylate/Steareth-20 Itaconate copolymer, and Acrylate/Celeth-20 Itaconate copolymer; Polystyrene sulphonate, copolymers of methacrylic acid and acrylamidomethylpropane sulfonic acid, and copolymers of acrylic acid and acrylamidomethylpropane sulfonic acid; carboxymethycellulose; carboxy guar; copolymers of ethylene and maleic acid; and acrylate silicone polymer. Neutralizing agents may be included to neutralize the anionic emulsifiers herein. Non-limiting examples of such neutralizing agents include sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, and mixtures thereof. Commercially available anionic emulsifiers include, for example, Carbomer supplied from Noveon under the tradename Carbopol 981 and Carbopol 980; Acrylates/C10-30 Alkyl Acrylate Crosspolymer having tradenames Pemulen TR-1, Pemulen TR-2, Carbopol 1342, Carbopol 1382, and Carbopol ETD 2020, all available from Noveon; sodium carboxymethylcellulose supplied from Hercules as CMC series; and Acrylate copolymer having a tradename Capigel supplied from Seppic. In another embodiment, anionic emulsifiers are carboxymethylcelluloses.

Polyacrylate Microcapsules

Various processes for microencapsulation, and exemplary methods and materials, are set forth in U.S. Pat. No. 6,592, 990; U.S. Pat. No. 2,730,456; U.S. Pat. No. 2,800,457; U.S. Pat. No. 2,800,458; and U.S. Pat. No. 4,552,811. Each patent described throughout this application is incorporated herein by reference to the extent each provides guidance regarding microencapsulation processes and materials.

The present invention teaches a low permeability microcapsule comprising a core material and a wall material at least partially surrounding, and in another embodiment, completely surrounding, a core material. In the present invention, the polyacrylate microcapsules are benefit agent microcapsule particulates which encapsulate benefit agents by capsule wall materials comprised of polymers.

Capsule wall materials useful herein include, for example, those formed from melamine-formaldehyde or urea-formaldehyde condensates, melamine-resorcinol or urea-resorcinol condensates, as well as similar types of aminoplasts, gelatin, polyurethane, polyamide, polyolefin, polysaccaharide, protein, silicone, lipid, modified cellulose, gums, polyacrylate, polyphosphate, polystyrene, and polyesters, or combinations of these materials. In another embodiment, a wall material that provides low permeability is polyacrylate.

The benefit agents of said core may comprise a material selected from the group consisting of perfumes; brighteners; enzymes; perfumes; sensates in one aspect a cooling agent; attractants, anti-bacterial agents; dyes; pigments; bleaches; and mixtures thereof.

In one aspect of said polyacrylate microcapsules, said benefit agent may comprise an anti-dandruff agent. Suitable, non-limiting examples of anti-dandruff agents include: pyridinethione salts, azoles, selenium sulfide, particulate sulfur, and mixtures thereof. Other embodiments include pyridinethione salts, specifically the zinc salt of 1-hydroxy-2-pyridinethione (known as "zinc pyridinethione" or "ZPT"). Such anti-dandruff particulate should be physically and chemically compatible with the essential components of the composition, and should not otherwise unduly impair product stability, aesthetics or performance.

In addition to the anti-dandruff actives selected from polyvalent metal salts of pyrithione, the present invention may further comprise one or more anti-fungal or anti-microbial actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Examples of anti-microbials include itraconazole, ketoconazole, selenium sulphide and coal tar.

The polyacrylate microcapsules useful herein are those releasing the benefit agents for a period of time after initial application. Potential trigger mechanisms for release of the encapsulated benefit agents may include, but are not limited to, mechanical forces, dehydration, light, pH, temperature, or even changes in ionic strength.

Process of Making Anionic Polyacrylate Microcapsules

An anionic polyacrylate microcapsule can be formed by either: (1) coating an already formed microcapsule with an anionic emulsifier; or (2) adding the anionic emulsifier to the microcapsule during the microcapsule making process. Any known method for generating a microcapsule is useful herein. Example methods for making polyacrylate microcapsules are disclosed in U.S. Patent Application 61/328,949; U.S. Patent Application 61/328,954; U.S. Patent Application 61/328,962; and U.S. Patent Application 61/328,967.

In one embodiment, polyacrlyate microcapsules are formed from water in oil, or oil in water emulsifications. During the polyacrylate microcapsule making process, a first composition is prepared as an oil phase. The oil phase may comprise oil; an oil soluble or dispersible primary, secondary, or tertiary amine; a multifunctional acrylate or methacrylate monomer or oligomer; an oil soluble acid; an initiator, and combinations thereof. In one embodiment, a nitrogen blanket is employed while the solution is mixed. Gradually, the temperature is increased to create a first composition reaction product. After the first composition reaction product is formed, a second composition is added to the reaction product.

The second composition is prepared as a water phase. The water phase may comprise water; an emulsifier that may be water soluble or water dispersible polymer or copolymer; at least one water phase initiator; one or more of an alkali or alkali salt, and combinations thereof. By water phase initiator, it is meant that the initiator is soluble or dispersible in water.

The second composition is then added to the oil solution of the first composition reaction product. This addition creates an oil-in-water emulsion. The reaction of the first composition in the presence of the second composition results in the formation of a low permeability microcapsule wall. The emulsion is further heated for a time and temperature sufficient to decompose the free radicals which are present in either one or both of the oil and water phases.

Furthermore, the polymerization of the monomers and oligomers in the oil phase causes a precipitation of the polymerized material. The precipitation of microcapsule wall material forms at the interface of the water and oil phases.

The anionic polyacrylate microcapsule is contained in the composition at a level by weight of from about 0.01% to about 50%, from about 0.05% to about 10%, from about 0.1% to about 8%, or from about 0.25% to 3%.

The anionic polyacrylate microcapsules useful herein are those having a particle size of from about 1 micron to about 80 microns, from about 2 microns to about 50 microns, and from about 5 microns to about 30 microns.

A. Coating a Microcapsule

In one embodiment of the invention, the anionic emulsifier is added to an already formed polyacrylate microcapsule. The anionic emulsifier attaches to the surface of the microcapsule through hydrogen bonding, van der Waals forces, ionic interactions, hydrophobic interactions, or chemical reactions. In one aspect, the anionic emulsifier surrounds at least a part of the external surface of the polyacrylate microcapsule, or is physically or chemically bound to the external surface of the polyacrylate microcapsule.

B. Adding Anionic Emulsifier to a Microcapsule

In another embodiment, the anionic emulsifier associates with the microcapsule surface during the microcapsule making process. When making the microcapsule, the anionic emulsifier is solubilized in an aqueous phase, which may optionally contain a free radical initiator, prior to emulsification of the oil. The excess aqueous phase is then added to the oil phase to form an oil-in-water emulsion. The emulsion is then heated for a time and at a temperature sufficient to decompose the free radicals which are positioned in one or both of the oil and aqueous phases. Microcapsule wall material is thereby formed at the interface of the water and oil phases. In one embodiment, when the emulsifier is comprised of acrylate moieties, the emulsifier may become chemically bound to the interfacial wall material.

C. Forming the Premix

Once the anionic polyacrlyate microcapsule is formed by either formation step, the anionic polyacrylate microcapsule is added to a cationic deposition polymer to form a premix. It has been surprisingly found that the anionic charge on the polyacrylate microcapsule leads to the formation of a microstructure on the shell of the microcapsule when combined with a cationic deposition polymer in the premix. This premix exhibits anionic polyacrylate microcapsules that have a higher viscoelasticity to the hair than microcapsules without an anionic charge and specific cationic deposition polymer thus giving a benefit to the hair.

Slurry/Aggolmerate

In one embodiment, the anionic polyacrylate microcapsules are contained in a slurry. The slurry may be combined with an adjunct ingredient to form a composition, for example, a shampoo consumer product.

In one aspect, the slurry may comprise one or more processing aids, selected from the group consisting of water, aggregate inhibiting materials such as divalent salts; particle suspending polymers such as xanthan gum, guar gum, and caboxy methyl cellulose. In another embodiment, said processing aids may be selected from the group consisting of amphoteric surfactants such as cocamidopropyl betaine (CAPB), zwitterionic surfactants, cationic swellable polymers, latex particles such as acrylic based ester Rheovis CDE, and mixtures thereof.

In one aspect, the slurry may comprise a carrier selected from the group consisting of polar solvents, including but not limited to, water, ethylene glycol, propylene glycol, polyethylene glycol, glycerol; nonpolar solvents, including but not limited to, mineral oil, perfume raw materials, silicone oils, hydrocarbon paraffin oils, and mixtures thereof.

In another embodiment, the anionic polyacrylate microcapsules are contained in an agglomerate with a second material. In one aspect, said second materials may comprise a material selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof.

Cationic Deposition Polymer

The shampoo composition of the present invention comprises a cationic deposition polymer that forms a premix when added to the anionic polyacrylate microcapsules. Any known natural or synthetic cationic deposition polymer can be used herein. Examples include those polymers disclosed in U.S. Pat. No. 6,649,155; U.S. patent application Ser. No. 12/103,902; U.S. Patent Publication 2008/0206355; and U.S. Patent Publication No. 2006/0099167A1.

The cationic deposition polymer is included in the composition at a level from about 0.01% to about 2%, in one embodiment from about 1.5% to about 1.9%, in another embodiment from about 1.8% to about 2.0%, in view of providing the benefits of the present invention.

The cationic deposition polymer is a water soluble polymer with a charge density from about 0.5 milliequivalents per gram to about 12 milliequivalents per gram. The cationic deposition polymer used in the composition has a molecular weight of about 100,000 Daltons to about 5,000,000 Daltons. The cationic deposition polymer is a low charge density cationic polymer.

In one embodiment, the cationic deposition polymer is a synthetic cationic deposition polymer. A variety of synthetic cationic deposition polymers can be used including mono- and di-alkyl chain cationic surfactants. In one embodiment, mono-alkyl chain cationic surfactants are chosen including, for example, mono-alkyl quaternary ammonium salts and mono-alkyl amines. In another embodiment, di-alkyl chain cationic surfactants are used and include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, and mixtures thereof.

In another embodiment, the cationic deposition polymer is a naturally derived cationic polymer. The term, "naturally derived cationic polymer" as used herein, refers to cationic deposition polymers which are obtained from natural sources. The natural sources may be polysaccharide polymers. Therefore, the naturally derived cationic polymer may be selected from the group comprising starches, guar, cellulose, Cassia, locust bean, Konjac, Tara, galactomannan, tapioca, and synthetic polymers. In a further embodiment, cationic deposition polymers are selected from Mirapol 100S (Rhodia), Jaguar C17, polyDADMAC, Tapioca starch (Akzo), polyTriquat, and mixtures thereof.

Forming a Premix

The cationic deposition polymer and the anionic polyacrylate microcapsule are mixed to form a premix before addition to the detersive composition comprising a detersive surfactant and a carrier.

The weight ratio of the anionic polyacrylate microcapsule to the cationic deposition polymer (based on the dry weight of the anionic microcapsules and the dry weight of the cationic deposition polymer) is from about 0.5:30 to about 20:1, from about 5:15 to about 15:1, and from about 5:1 to about 12:1. It is believed that too much cationic polymer may not provide enhanced and/or prolonged benefits to the benefit agent microcapsules due to the formation of excess cationic polymer coating on the capsule wall. This excess coating may prevent the microcapsule wall from breaking and releasing the benefit agents.

Microcapsules and anionic emulsifiers may be dispersed in solvents such as water while mixing with the cationic deposition polymer. In one embodiment, the amount of water present is from about 90% to about 50%, in another embodiment from about 70% to about 50%, and in another embodiment from about 60% to about 50%. In another embodiment of the invention, the anionic emulsifiers associate with the microcapsule walls to form anionic polyacrylate microcapsules prior to their mixing with cationic deposition polymers.

Detersive Composition

The detersive composition can be all aqueous phase or may comprise both an oil phase and an aqueous phase. In one embodiment, the detersive composition has both an oil phase and an aqueous phase. After being added to the detersive composition, the polyacrylate microcapsules reside in the aqueous phase of such embodiments.

The detersive composition may comprise any combination of the following components:

A. Detersive Surfactant

The shampoo composition of the present invention includes a detersive surfactant. The detersive surfactant provides cleaning performance to the composition. The detersive surfactant in turn comprises anionic detersive surfactant, zwitterionic or amphoteric detersive surfactant, or combinations thereof. Various examples and descriptions of detersive surfactants are set forth in U.S. Pat. No. 6,649,155; U.S. patent application Ser. No. 12/103,902; and U.S. Patent Publication 2008/0206355, and are incorporated herein for reference.

The concentration of the anionic surfactant component in the shampoo should be sufficient to provide the desired cleaning and lather performance, and generally ranges from about 2% to about 50%, from about 8% to about 30%, from about 10% to about 25%, or from about 12% to about 22%.

Anionic surfactants suitable for use in the compositions are the alkyl and alkyl ether sulfates. Other suitable anionic detersive surfactants are the water-soluble salts of organic, sulfuric acid reaction products. Still other suitable anionic detersive surfactants are the reaction products of fatty acids esterified with isethionic acid and neutralized with sodium hydroxide. Other similar anionic surfactants are described in U.S. Pat. Nos. 2,486,921; 2,486,922; and 2,396,278.

Anionic detersive surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment of the present invention, the anionic surfactant is sodium lauryl sulfate or sodium laureth sulfate.

Suitable amphoteric or zwitterionic detersive surfactants for use in the shampoo composition herein include those which are known for use in hair care or other personal care cleansing. Concentrations of such amphoteric detersive surfactants range from about 0.5% to about 20%, and from about 1% to about 10%. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378.

B. Anti-Dandruff Actives

The shampoo compositions of the present invention may also contain an anti-dandruff agent. Suitable, non-limiting examples of anti-dandruff agents include: antimicrobial actives, pyridinethione salts, azoles, selenium sulfide, particulate sulfur, keratolytic acid, salicylic acid, octopirox (piroctone olamine), coal tar, and combinations thereof. In one aspect, the anti-dandruff agents typically are pyridinethione salts. Such anti-dandruff agents should be physically and chemically compatible with the essential components of the composition, and should not otherwise unduly impair product stability, aesthetics or performance.

Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

C. Aqueous Carrier

The formulations of the present invention can be in the form of pourable liquids (under ambient conditions). Such compositions will therefore typically comprise an aqueous carrier, which is present at a level of from about 20% to about 95%, or even from about 60% to about 85%. The aqueous carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

The carrier useful in the present invention includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

D. Other Optional Components

The shampoo composition may further comprise other optional ingredients that are known for use or otherwise useful in compositions. Such optional ingredients are most typically those described in reference books such as the CTFA Cosmetic Ingredient Handbook, Second Edition, The Cosmetic, Toiletries, and Fragrance Association, Inc. 1988, 1992.

Further non-limiting examples of such optional ingredients include perfumes or fragrances, coloring agents or dyes, hair bleaching agents, thickeners, moisturizers, emollients, pharmaceutical actives, vitamins or nutrients, anti-dandruff agents, perfumes, hair colorants, hair perming agents, hair growth or restorer agents, and similar other materials.

Method of Manufacture

The shampoo compositions of the present invention can be prepared by the process comprising: 1) coating a polyacrylate microcapsule with an anionic emulsifier to form an anionic polyacrylate microcapsule; 2) combining the anionic polyacrylate microcapsule with a cationic deposition polymer to form a premix; and 3) adding the premix to a detersive composition comprising surfactant and a carrier.

In another embodiment, the shampoo compositions of the present invention can be prepared by the process comprising: 1) coating a polyacrylate microcapsule with an anionic emulsifier to form an anionic polyacrylate microcapsule; 2) combining the anionic polyacrylate microcapsule with a cationic deposition polymer to form a premix; 3) adding the premix to a anionic surfactant; and 4) adding the resulting composition of step (3) to a detersive composition comprising surfactant and a carrier.

It has been unexpectedly found that the association of anionic polyacrylate microcapsules combined with cationic deposition polymers has a higher viscoelasticity than in the absence of the mixed components thus giving a better adhesion of the anionic microcapsules to the hair.

For example, when an anionic emulsifier comprising a copolymer of acrylic acid and butyl acrylate (molecular weight of 40,000 g/mol), is mixed with various cationic polymers to form a polymer premix, the result is a significant increase in viscoelasticity. This increase indicates a strong polyelectrolyte interaction which is exemplified in the increase in viscoelastic component G' as the quantity of cationic polymer increases (See Table 1)

TABLE 1

Viscoelasticity as a function of anionic:cationic polymer premix ratio.

| Sample Description | Anionic Emulsifier (wt %) | Cationic Polymer (wt %) | Anionic Surfactant (wt %) | G' at 1 Hz (Pascals) | G" at 1 Hz (Pascals) |
|---|---|---|---|---|---|
| 1:5 Anionic:Cationic | 5.10% | 25.48% | 0.00% | 0.369 | 6.55 |
| 1:10 Anionic:Cationic | 2.78% | 27.79% | 0.00% | 0.178 | 7.22 |
| 1:20 Anionic:Cationic | 1.46% | 29.12% | 0.00% | 0.233 | 7.92 |

Furthermore, when an anionic surfactant is added to the polymer premix, a substantial increase in viscoelasticity is also noted. Such an increase in viscoelasticity is influenced by the strength of the association between the cationic deposition polymer and the anionic surfactant. This is exemplified in the increase in viscoelastic component G' upon addition of anionic surfactant to the premix (See Table 2).

TABLE 2

Viscoelasticity as a function of anionic surfactant addition to polymer premix.

| Sample ID | Anionic Emulsifier | Cationic Polymer | Anionic Surfactant | G' at 1 Hz (Pascals) | G" at 1 Hz (Pascals) |
|---|---|---|---|---|---|
| 1:5 Anionic:Cationic | 3.05% | 15.25% | 10.87% | 42 | 105.6 |
| 1:10 Anionic:Cationic | 1.65% | 16.48% | 11.74% | 37.1 | 7.1 |
| 1:20 Anionic:Cationic | 0.86% | 17.17% | 12.23% | 118.2 | 133.9 |

In one embodiment of the invention, an anionic emulsifier is covalently bonded to the outer wall of the polyacrylate microcapsule by incorporating the anionic emulsifier during the microcapsule making process. In another embodiment, the anionic emulsifier is added to the slurry comprising a fully formed polyacrylate microcapsule. After forming the anionic polyacrylate microcapsule through either step, a cationic deposition polymer is then added to the anionic microcapsule to form a viscoelastic premix. When this premix is then combined with an anionic surfactant, an association of polymers forms a microstructure on the anionic polyacrylate microcapsule wall. The microstructure forms upon dilution of the shampoo composition. Once formed, the high viscosity of the polymer association microstructure results in an anionic polyacrylate microcapsule that maintains its microcapsule structure even upon dilution of the shampoo during washing. In addition, the microcapsule structure provides multiple points of contact to the substrate which works to resist rinse-off of the microcapsules during the use of the shampoo composition.

The polyacrylate microcapsules of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

Any suitable method of making the shampoo of the present invention may be used non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

Product Forms

The shampoo compositions of the present invention can be in the form of rinse-off products or leave-on products, and can be formulated in a wide variety of product forms, including but not limited to creams, gels, emulsions, mousses and sprays.

In one embodiment, the shampoo composition is in the form of a gel comprising less than about 45% water. In such embodiment, the gel may have a neat viscosity of about 1,000 cps to about 10,000 cps. The neat viscosity of a gel can be defined as the viscosity of the fluid at a shear rate of 1/sec. Scientifically, viscosity is the ratio of shear stress to shear rate. In some embodiments, the range of shear rates for gels is from 0.01/sec to 10/sec.

Neat viscosity of the gel product form can be measured with a rheometer according to the following method:
(1) Load the sample onto the plate.
(2) Establish a gap of 1 millimeter between the 1 degree cone and the plate.
(3) Perform a shear sweep on the fluid from 0.01/sec to 10/sec.
(4) Record the shear stress response of the fluid.
(5) Determine the neat viscosity of the fluid by calculating the ratio of shear stress to shear rate at each shear rate.

Test Methods

It is understood that the test methods that are disclosed in the Test Methods Section of the present application should be used to determine the respective values of the parameters of Applicants' invention as such invention is described and claimed herein.

A. ClogP

The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor, and C. A. Ramsden, Eds. P. 295, Pergamon Press, 1990, incorporated herein by reference). ClogP values may be calculated by using the "CLOGP" program available from Daylight Chemical Information Systems Inc. of Irvine, Calif. U.S.A.

B. Boiling Point

Boiling point is measured by ASTM method D2887-04a, "Standard Test Method for Boiling Range Distribution of Petroleum Fractions by Gas Chromatography," ASTM International.

C. Median Particle Size

Particle size is measured using an Accusizer 780A, made by Particle Sizing Systems, Santa Barbara Calif. The instrument is calibrated from 0 to 300µ using Duke particle size standards. Samples for particle size evaluation are prepared by diluting about 1 g of capsule slurry in about 5 g of deionized water and further diluting about 1 g of this solution in about 25 g of water.

About 1 g of the most dilute sample is added to the Accusizer and the testing initiated, using the autodilution feature. The Accusizer should be reading in excess of 9200 counts/second. If the counts are less than 9200 additional sample should be added. The accusizer will dilute the test sample until 9200 counts/second and initiate the evaluation. After 2 minutes of testing the Accusizer will display the results, including volume-weighted median size.

The broadness index can be calculated by determining the particle size at which 95% of the cumulative particle volume is exceeded (95% size), the particle size at which 5% of the cumulative particle volume is exceeded (5% size), and the median volume-weighted particle size (50% size-50% of the particle volume both above and below this size). Broadness Index (5)=((95% size)-(5% size)/50% size).

D. Olfactive Analysis of Shampoo Product

Analysis steps include:
a. 0.4 millileters of Shampoo product is applied to a hair switch (1HI, 4 grams, 8 inches long, moderately damaged grade) that has been combed, wet, and lightly squeeged. Lather switch 50-60 strokes (30 seconds) in a milking action.
b. Rinse with stationary shower rinse with no manipulation of hair (100 degrees Fahrenheit water temperature, water flow at 1.5 gallons per minute, for 30 seconds, water hardness of 8 grains per gallon). Lightly squeegee once down the hair switch from top to bottom between fingers after rinsing to remove excess water.
c. Repeat application of product per step (a), milking, rinsing, and squeeging per step (b).
d. Leave hair to dry at ambient temperature by hanging it on a rack. After approximately 3 hours, olfactively grade the hair switch according to the Primavera Grade (0-100 scale for intensity, where a 10 point difference is consumer noticeable). Record this as the Initial Pre-Comb fragrance intensity.
e. Comb the hair switch 3 times and olfactively grade, record this as the Initial Post-Comb fragrance intensity.
f. Leave the hair switch under ambient conditions (70 degrees Fahrenheit and 30% relative humidity) for 24 hours. Then, olfactively grade the hair switch according to the Primavera Grade (0-100 scale for intensity, where a 10 point difference is consumer noticeable), record this as the 24 hr aged Pre-Comb olfactive intensity. Comb the hair switch 3 times and assign an olfactive grade, record this as the 24 hr aged Post-Comb olfactive intensity.

E. Fracture Strength Test Method

Analysis steps include:
a.) Place 1 gram of particles in 1 liter of distilled deionized (DI) water.
b.) Permit the particles to remain in the DI water for 10 minutes and then recover the particles by filtration, using a 60 mL syringe filter, 1.2 micron nitrocellulose filter (Millipore, 25 mm diameter).
c.) Determine the rupture force of 50 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the fracture strength of each particle by dividing the rupture force (in Newtons) by the cross-sectional area of the respective spherical particle ($\pi r^2$, where r is the radius of the particle before compression), said cross-sectional area being determined as follows: measuring the particle size of each individual particle using the experimental apparatus and method of Zhang, Z.; Sun, G; "Mechanical Properties of Melamine-Formaldehyde microcapsules," J. Microencapsulation, vol 18, no. 5, pages 593-602, 2001.
d.) Use the 50 independent measurements from c.) above, and calculate the percentage of particles having a fracture strength within the claimed range fracture strength range.

F. Zeta Potential (1) Equipment specifications: Malvern Zeatasizer Nano Model ZEN3600 Sample cell, disposable capillary cell (green cell)
(2) Use Duke standards to measure the PSD, and use it to measure the zeta potential to assure that the instrument is functioning properly.
(3) Flush a DTS1060 capillary cell with 1-2 mL ethanol, the with DI water to prepare the capillary cell.
(4) Sample preparation: first, filter 20 mL DI water through 0.2 micron filter into a 20 mL vial. Add 1 drop (50 microliters of 30 wt % solids particulate suspension into the vial and invert the sample back and forth gently until the particulate suspension is homogeneously dispersed in the vial. Next, rinse a DTS1060 green disposable zeta cell with 1-2 mL of DI water, then use a syringe to transfer the sample solution from the vial into the zeta cell, making sure that no air bubbles are present in the cell. Fill the cell to the top, then place a cap on the cell outlet and inlet (again making sure no air bubbles are present in the sample cell). Then, place the cell in the sample chamber, with the electrodes facing the sides of the system. Finally, place the sample cell in the instrument.
(5) Conditions for the run:
a. Refractive index=1.35 (this number may vary for suspensions. One can measure the refractive index for any particulate suspension using a refractometer)
b. Temperature=25 degrees Centigrade
c. Equilibration time=1 minute
d. Smoluchowski model to be used to calculate the zeta potential
(6) Measure each sample in triplicate. The result from the instrument is reported as Zeta Potential in milliVolts, with no extrapolation.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

A perfume composition, called Scent A, is utilized to prepare the examples of the invention. The table below lists the ingredients, and their properties. Table 2 provides the ClogP breakdown of the perfume oil composition.

TABLE 1

| Material Name | ClogP | Boiling Point ° C. |
| --- | --- | --- |
| Beta Gamma Hexenol | 1.3 | 155 |
| Phenyl Ethyl Alcohol | 1.32 | 219 |
| Helional | 1.77 | 329 |
| Triplal Extra | 1.78 | 199 |
| Amyl- Acetate (isomer Blends) | 1.87 | 135 |
| Melonal | 2.09 | 182 |
| Liffarome | 2.14 | 167 |
| Iso Eugenol Acetate | 2.17 | 303 |
| Cis 3 Hexenyl Acetate | 2.18 | 167 |
| Jasmolactone | 2.36 | 219 |
| 2'6-nonadien-1-ol | 2.43 | 213 |
| Florasa | 2.46 | 238 |
| Nonalactone | 2.66 | 193 |
| Cis Jasmone | 2.81 | 254 |
| Ethyl Linalool | 2.92 | 223 |
| Pino Acetaldehyde | 2.98 | 261 |
| Methyl Dihydro Jasmonate | 3.01 | 323 |
| Undecavertol | 3.06 | 242 |
| Azurone 10/tec 0015573 | 3.06 | 395 |
| Dihydro Myrcenol | 3.08 | 195 |
| Cyclemax | 3.23 | 281 |
| Hivernal | 3.29 | 351 |
| Pomarose | 3.51 | 214 |
| Undecalactone | 3.75 | 228 |
| Damascenone Total 937459 | 3.89 | 267 |
| Acalea (01-1963) | 3.9 | 344 |
| Cis-3-hexenyl Salicylate | 4 | 316 |

TABLE 1-continued

| Material Name | ClogP | Boiling Point ° C. |
|---|---|---|
| Ionone Beta | 4.02 | 267 |
| Polysantol | 4.21 | 256 |
| Ambroxan | 4.58 | 285 |
| 5-cyclohexadecen-1-one | 5.04 | 331 |
| Iso E Super Or Wood | 5.05 | 325 |
| Laevo Muscone | 5.48 | 321 |
| Helvetolide 947650 | 5.56 | 309 |

Example 1

Nonionic Microcapsule (TAS0810101, MVF1837-94B)

An oil solution, consisting of 75 g Fragrance Oil scenta, 75 g of Isopropyl Myristate, 0.6 g DuPont Vazo-52, and 0.4 g DuPont Vazo-67, is added to a 35° C. temperature controlled steel jacketed reactor, with mixing at 1000 rpm (4 tip, 2" diameter, flat mill blade) and a nitrogen blanket applied at 100 cc/min. The oil solution is heated to 75° C. in 45 minutes, held at 75° C. for 45 minutes, and cooled to 60° C. in 75 minutes.

A second oil solution, consisting of 37.5 g Fragrance Oil, 0.5 g tertiarybutylaminoethyl methacrylate, 0.4 g 2-carboxyethyl acrylate, and 20 g Sartomer CN975 (hexafunctional urethane-acrylate oligomer) is added when the first oil solution reached 60° C. The combined oils are held at 60° C. for an additional 10 minutes.

Mixing is stopped and a water solution, consisting of 56 g of 5% active polyvinyl alcohol Celvol 540 solution in water, 244 g water, 1.1 g 20% NaOH, and 1.2 g DuPont Vazo-68WSP, is added to the bottom of the oil solution, using a funnel.

Mixing is again started, at 2500 rpm, for 60 minutes to emulsify the oil phase into the water solution. After milling is completed, mixing is continued with a 3" propeller at 350 rpm. The batch is held at 60° C. for 45 minutes, the temperature is increased to 75° C. in 30 minutes, held at 75° C. for 4 hours, heated to 90° C. in 30 minutes and held at 90° C. for 8 hours. The batch is then allowed to cool to room temperature. The finished microcapsules have a median particle size of 6.4 microns, a broadness index of 1.3, and a zeta potential of negative 0.5 millivolts.

Example 2

Anionic Microcapsule, Large Particle Size (TAS1122101)

Capsules are made using identical materials, compositions, and process conditions as in Example 1 with the following exceptions: 1 gram of Vazo-52, 0.8 grams of Vazo-67, 0.3 grams of tertiarybutylaminoethyl methacrylate, 0.25 grams of 2-carboxyethyl acrylate, and 12 grams of Sartomer CN975 as compositional differences in the oil phase; and 22 grams of 25% active Colloid 351, and 308 grams of water as compositional differences in the water phase. All other mixing and process conditioner remains the same. The finished microcapsules have a median particle size of 10.7 microns, a broadness index of 1.5, and a zeta potential of negative 60 millivolts.

Example 3

Anionic Microcapsule, Small Particle Size (TAS1123101)

Capsules are made using identical materials, compositions, and process conditions as in Example 1 with the following exceptions: 1 gram of Vazo-52, 0.8 grams of Vazo-67, 1.5 grams of tertiarybutylaminoethyl methacrylate, 1.2 grams of 2-carboxyethyl acrylate, and 60 grams of Sartomer CN975 as compositional differences in the oil phase; and 68 grams of 25% active Colloid 351, and 282 grams of water as compositional differences in the water phase. All other mixing and process conditioner remains the same. The finished microcapsules have a median particle size of 1.4 microns, a broadness index of 1.2, and a zeta potential of negative 60 milivolts.

Example 4

Cationic Microcapsule (TAS0204101)

An oil solution, consisting of 112.5 g Fragrance Oil Scent A, 37.5 g of Isopropyl Myristate, 0.6 g DuPont Vazo-52, and 0.4 g DuPont Vazo-67, is added to a 35° C. temperature controlled steel jacketed reactor, with mixing at 1000 rpm (4 tip, 2" diameter, flat mill blade) and a nitrogen blanket applied at 100 cc/min. The oil solution is heated to 75° C. in 45 minutes, held at 75° C. for 45 minutes, and cooled to 60° C. in 75 minutes.

A second oil solution, consisting of 37.5 g Fragrance Oil, 0.5 g tertiarybutylaminoethyl methacrylate, 0.4 g 2-carboxyethyl acrylate, and 20 g Sartomer CN975 (hexafunctional urethane-acrylate oligomer) is added when the first oil solution reached 60° C. The combined oils are held at 60° C. for an additional 10 minutes.

Mixing is stopped and a water solution, consisting of 5.6 g of poly(dimethylamine-co-epichlorohydrin-co-ethylenediamine) and 360 grams of water, 2.8 g 20% NaOH, and 1.2 g DuPont Vazo-68WSP, is added to the bottom of the oil solution, using a funnel.

Mixing is again started, at 2500 rpm, for 60 minutes to emulsify the oil phase into the water solution. After milling is completed, mixing is continued with a 3" propeller at 350 rpm. The batch is held at 60° C. for 45 minutes, the temperature is increased to 75° C. in 30 minutes, held at 75° C. for 4 hours, heated to 90° C. in 30 minutes and held at 90° C. for 8 hours. The batch is then allowed to cool to room temperature. The finished microcapsules have a median particle size of 10.5 microns, a broadness index of 1.3, and a zeta potential of 25 millivolts.

Example 5

Anionic Microcapsule (TAS1101101)

Capsules are made using identical materials, compositions, and process conditions as in Example 2 with the following exceptions: 1 gram of tertiarybutylaminoethyl methacrylate, 0.8 grams of 2-carboxyethyl acrylate, and 40 grams of Sartomer CN975 as compositional differences in the oil phase; and 22 grams of 25% active Colloid 351, and 282 grams of water as compositional differences in the water phase. All other mixing and process conditioner remains the same. The finished microcapsules have a median particle size of 4.8 microns, a broadness index of 1.3, and a zeta potential of negative 60 milivolts.

Example 6

Microcapsule with Cationic Polymer Emulsifier

Capsules are made using identical materials, compositions, and process conditions as in Example 1 with the following exceptions: 20 grams of 32% active poly(diallyl dimethyl ammonium chloride) added to the water phase, along with 236 grams of water. All other mixing and process conditioner remains the same. The finished microcapsules have a median particle size of 9 microns, and a broadness index of 1.3, and a zeta potential of 38 millivolts.

Example 7

Shampoo Composition

| Ingredient | EXAMPLE COMPOSITION | | |
|---|---|---|---|
| | I | II | III |
| Water | q.s. | q.s. | q.s. |
| Polyquaternium 76 [1] | 2.50 | — | — |
| Guar, Hydroxylpropyl Trimonium Chloride [2] | — | 0.25 | — |
| Polyquaterium 6 [3] | — | — | 0.79 |
| Sodium Laureth Sulfate (SLE3S) [4] | 21.43 | 21.43 | 21.43 |
| Sodium Lauryl Sulfate (SLS) [5] | 20.69 | 20.69 | 20.69 |
| Silicone [6] | 0.75 | 1.00 | 0.5 |
| Cocoamidopropyl Betaine [7] | 3.33 | 3.33 | 3.33 |
| Cocoamide MEA [8] | 1.0 | 1.0 | 1.0 |
| Ethylene Glycol Distearate [9] | 1.50 | 1.50 | 1.50 |
| Sodium Chloride [10] | 0.25 | 0.25 | 0.25 |
| Fragrance | 0.70 | 0.70 | 0.70 |
| Preservatives, pH adjusters | Up to 1% | Up to 1% | Up to 1% |

[1] Mirapol AT-1, Copolymer of Acrylamide(AM) and TRIQUAT, MW = 1,000,000; CD = 1.6 meq./gram; 10% active; Supplier Rhodia
[2] Jaguar C500, MW—500,000, CD = 0.7, supplier Rhodia
[3] Mirapol 100S, 31.5% active, supplier Rhodia
[4] Sodium Laureth Sulfate, 28% active, supplier: P&G
[5] Sodium Lauryl Sulfate, 29% active supplier: P&G
[6] Glycidol Silicone VC2231-193C
[7] Tegobetaine F-B, 30% active supplier: Goldschmidt Chemicals
[8] Monamid CMA, 85% active, supplier Goldschmidt Chemical
[9] Ethylene Glycol Distearate, EGDS Pure, supplier Goldschmidt Chemical
[10] Sodium Chloride USP (food grade), supplier Morton; note that salt is an adjustable ingredient, higher or lower levels may be added to achieve target viscosity.

| Ingredient | EXAMPLE COMPOSITION | |
|---|---|---|
| | IV | V |
| Sodium Laureth Sulfate | 10.00 | 10.00 |
| Sodium Lauryl Sulfate | 1.50 | 1.50 |
| Cocamidopropyl betaine | 2.00 | 2.00 |
| Guar Hydroxypropyl trimonium chloride (1) | 0.40 | |
| Guar Hydroxypropyl trimonium chloride (2) | | 0.40 |
| Dimethicone (3) | 2.00 | 2.00 |
| Gel Network (4) | | 27.27 |
| Ethylene Glycol Distearate | 1.50 | 1.50 |
| 5-Chloro-2-methyl-4-isothiazolin-3-one, Kathon CG | 0.0005 | 0.0005 |
| Sodium Benzoate | 0.25 | 0.25 |
| Disodium EDTA | 0.13 | 0.13 |
| Perfume | 0.40 | 0.40 |
| Citric Acid/Sodium Citrate Dihydrate | pH QS | pH QS |
| Sodium Chloride/Ammonium Xylene Sulfonate | Visc. QS | Visc. QS |
| Water | QS | QS |

(1) Jaguar C17 available from Rhodia
(2) N-Hance 3269 (with Mol. W. of ~500,000 and 0.8 meq/g) available from Aqulaon/Hercules
(3) Viscasil 330M available from General Electric Silicones
(4) Gel Networks; See Composition below. The water is heated to about 74° C. and the Cetyl Alcohol, Stearyl Alcohol, and the SLES Surfactant are added to it. After incorporation, this mixture is passed through a heat exchanger where it is cooled to about 35° C. As a result of this cooling step, the Fatty Alcohols and surfactant crystallized to form a crystalline gel network.

| Ingredient | Wt. % |
|---|---|
| Water | 86.14% |
| Cetyl Alcohol | 3.46% |
| Steary Alcohol | 6.44% |
| Sodium laureth-3 sulfate (28% Active) | 3.93% |
| 5-Chloro-2-methyl-4-isothiazolin-3-one, Kathon CG | 0.03% |

Example 8

Shampoo with No Premixing of Capsules

Perfume and/or perfume microcapsules disclosed in the above examples are added on top of a pre-made shampoo formula with a 10 wt % formula hole (shampoo compositions of Example 7 II, formulations with 10% hole). The table below lists the masses of the various ingredients. The mixture is then speed mixed at 1900 RPM for 1 minute using a DAFC 400FVZ speed mixer. The Olfactive Analysis of Shampoo Product test method is utilized to grade hair treated with the prepared shampoo compositions. These results are presented below.

| Example Reference | PMC Example ID | Mass of Microcapsule or Perfume (g) | Mass of Shampoo (g) | Mass of Water (g) | 4 hr (Pre/Post-Comb) | 24 hr (Pre/Post-Comb) |
|---|---|---|---|---|---|---|
| 8A | Scent A | 0.50 | 90.0 | 9.50 | 10/10 | 0/0 |
| 8B | 1 | 1.81 | 90.0 | 8.19 | 10/15 | 0/0 |
| 8C | 2 | 1.43 | 90.0 | 8.57 | 10/15 | 0/0 |
| 8D | 3 | 2.42 | 90.0 | 7.58 | 10/15 | 0/0 |
| 8E | 4 | 1.48 | 90.0 | 8.52 | 10/10 | 0/0 |
| 8F | 5 | 2.13 | 90.0 | 7.87 | 10/10 | 0/0 |
| 8G | 6 | 2.39 | 90.0 | 7.61 | 0/0 | 0/0 |

Example 9

Shampoo with Premixing of Capsules

The perfume microcapsules of Examples 1 through 6 are first premixed with polyDADMAC (polydiallyl dimethyl ammonium chloride, Mirapol 100S from Rhodia) by pre-weighing the perfume microcapsules in a jar, then adding the Mirapol 100S, followed by the addition of water. The contents are then mixed at 1950 RPM for 1 minutes using a Hausfeld DAFC 400FVZ speed mixer to achieve a homogeneous suspension of microcapsules. The masses of materials that are premixed are recorded in the table below. The polymer to perfume ratio in the premix is maintained at 1:5 for all of the samples, and the amount of Mirapol 100S polymer is maintained at 0.10 wt % in the finished shampoo formulation.

| Premix ID | PMC Example ID | Mass of Microcapsule | Mass of Mirapol 100S Polymer (31.5% active) | Mass of Water (g) | Final Perfume Content wt % |
|---|---|---|---|---|---|
| 9A | 1 | 10.87 | 1.90 | 7.23 | 15% |
| 9B | 2 | 8.60 | 1.90 | 9.50 | 15% |
| 9C | 3 | 14.49 | 1.90 | 3.60 | 15% |
| 9D | 4 | 8.89 | 1.90 | 9.20 | 15% |
| 9E | 5 | 12.77 | 1.90 | 5.33 | 15% |
| 9F | 6 | 14.32 | 1.90 | 3.77 | 15% |

The cationic polymer/microcapsule premixes are then formulated into a shampoo (example compositions provided in Example 7 II, a formulation with 10% hole was utilized) by preweighing the shampoo in a jar, then adding the premix, followed by addition of water, and then mixing at 1950 RPM for 1 minute using a Hausfeld DAFC 400FVZ Speed Mixer to achieve a homogeneous product.

The Olfactive Analysis of Shampoo Product test method is utilized to grade hair treated with the prepared shampoo compositions. These results are presented below.

| Example Reference | PMC Example ID | Mass of Microcapsule or Perfume (g) | Mass of Shampoo (g) | Mass of Water (g) | 4 hr (Pre/Post-Comb) | 24 hr (Pre/Post-Comb) |
|---|---|---|---|---|---|---|
| 9G | Scent A | 0.50 | 90.0 | 9.50 | 10/10 | 0/0 |
| 9H: Nonionic | 1 | 3.33 | 90.0 | 6.67 | 10/15 | 0/0 |
| 9I: Anionic | 2 | 3.33 | 90.0 | 6.67 | 25/35 | 10/20 |
| 9J: Anionic | 3 | 3.33 | 90.0 | 6.67 | 30/45 | 10/40 |
| 9K: Cationic | 4 | 3.33 | 90.0 | 6.67 | 10/10 | 0/0 |
| 9L: Anionic | 5 | 3.33 | 90.0 | 6.67 | 40/50 | 20/40 |
| 9M: Cationic | 6 | 3.33 | 90.0 | 6.67 | 5/5 | 0/0 |

Note that the anionic microcapsules provide the best olfactive results.

Example 10

Cationic Polymer Level Study

Anionic microcapsules of Example 5 are premixed with various amounts of polyDADMAC (Mirapol 100S, Rhodia), see table below. These premixes are agitated at 1950 RPM for 1 minute using a Hausfeld 400 FVZ Speed Mixer. The premixes are then added to shampoo of Example 7 II (formulation with 10% hole), and formulation balanced to 100% with the addition of water. The shampoo mixture is then agitated at 1950 RPM for 1 minute using a Hausfeld 400 FVZ Speed Mixer.

The Olfactive Analysis of Shampoo Product test method is utilized to grade hair treated with the prepared shampoo compositions. These results are presented below.

| Sample ID | Shampoo Premix (g) | Mirapol 100S (g) | Microcapsule of Example 5 (g) | Deionized Water (g) | 4 hr Pre/Post Comb | 24 hr Pre/Post Comb |
|---|---|---|---|---|---|---|
| 10A | 90 | 0 | 0.00 | 9.5 | 10/15 | 0/0 |
| 10B | 90 | 0.00 | 2.00 | 8.01 | 30/35+ | 10/20 |
| 10C | 90 | 0.32 | 2.00 | 7.69 | 40+/55+ | 20/40 |
| 10D | 90 | 0.79 | 2.00 | 7.22 | 40/45+ | 10/30+ |
| 10E | 90 | 1.59 | 2.00 | 6.42 | 40/55 | 10/35 |
| 10F | 90 | 3.17 | 2.00 | 4.84 | 40/60+ | 20+/35+ |
| 10G | 90 | 6.32 | 2.00 | 1.68 | 10/15+ | 5/10 |

Notice that very low levels of polymer are required for pre-mixing with the microcapsules to achieve the desired interaction and delivery efficiency.

Example 11

A Variety of Cationic Polymers mixed with Anionic Microcapsules

Anionic microcapsules of Example 5 are premixed with a variety of cationic polymers, see table below. The powder polymers (100% active in the table below) are first mixed with water at 1950 RPM for 1 minute using a Hausfeld 400 FVZ Speed Mixer. In the case of Tapioca starch, the dispersion is also heated. Subsequently, anionic microcapsules of Example 5 are added to the polymer solutions in water, and these premixes are agitated at 1950 RPM for 1 minute using a Hausfeld 400 FVZ Speed Mixer. The premixes are then added to shampoo of Example 7 II, and formulation balanced to 100% with the addition of water. The shampoo mixture is then agitated at 1950 RPM for 1 minute using a Hausfeld 400 FVZ Speed Mixer.

The Olfactive Analysis of Shampoo Product test method is utilized to grade hair treated with the prepared shampoo compositions. These results are presented below.

Polymer Premix Preparation

| Sample ID | Polymer Type | Polymer Activity % | Anionic Microcapsule of Example 5 (g) | Polymer (g) | Water (g) | Final Perfume wt % |
|---|---|---|---|---|---|---|
| 11A | Mirapol 100S | 31.50% | 12.43 | 1.85 | 5.72 | 14.60% |
| 11B | 70:30 Guar:Aptac | 100.00% | 12.43 | 0.58 | 6.99 | 14.60% |
| 11C | HMW, HCD Guar:Maptac | 88.00% | 12.43 | 0.66 | 6.91 | 14.60% |
| 11D | Triquat | 15.50% | 12.43 | 3.77 | 3.81 | 14.60% |
| 11E | Jaguar C17 | 100.00% | 12.43 | 0.58 | 6.99 | 14.60% |
| 11F | Tapioca | 100.00% | 12.43 | 0.58 | 6.99 | 14.60% |

Shampoo preparation and olfactive analysis

| Sample ID | Polymer Type | Perfume Technology (PDT) | Shampoo Mass (g) | PDT Mass (g) | Water (g) | 4 hr Pre/Post Comb | 24 hr Pre/Post Comb |
|---|---|---|---|---|---|---|---|
| 11G | None | Scent A | 45.00 | 0.250 | 4.750 | 25/25 | 10/10 |
| 11H | None | Example 5 | 45.00 | 1.064 | 3.936 | 15+/15+ | 10/10 |
| 11I | Mirapol 100S | 11A | 45.00 | 1.712 | 3.288 | 35+/50 | 20+/35 |
| 11G | 70:30 Guar:Aptac | 11B | 45.00 | 1.712 | 3.288 | 30+/45+ | 20+/35 |
| 11H | HMW, HCD Guar:Maptac | 11C | 45.00 | 1.712 | 3.288 | 25/35+ | 10/30 |
| 11I | Triquat | 11D | 45.00 | 1.712 | 3.288 | 30+/60 | 20+/45 |
| 11J | Jaguar C17 | 11E | 45.00 | 1.712 | 3.288 | 30/70 | 10+/55 |
| 11K | Tapioca | 11F | 45.00 | 1.712 | 3.288 | 35+/60 | 10/45 |

Note that the choice of polymer is critical in achieving a favorable interaction between the microcapsule, cationic deposition polymer, and the shampoo formulation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A shampoo composition comprising:
   (a) a premix, the premix comprising from about 0.001% to about 10%, by weight of the shampoo composition, of an anionic charged polyacrylate microcapsule, wherein the anionic charged polyacrylate microcapsule comprises an anionic emulsifier and a polyacrylate microcapsule and from about 0.01% to about 2%, by weight of the composition of a cationic deposition polymer;
   (b) from about 2% to about 25%, by weight of the shampoo composition, of a detersive surfactant; and
   (c) a carrier.

2. The shampoo composition of claim 1, wherein the anionic charged polyacrylate microcapsule are made by adding the anionic emulsifier to the polyacrylate microcapsule during the polacrylate microcapsule making process.

3. The shampoo composition of claim 1, wherein the anionic charged polyacrylate microcapsule and the cationic deposition polymer are mixed such that the weight ratio of the anionic charged polyacrylate microcapsule to the cationic deposition polymer is from about 1.0:0.01 to about 1.0:10.

4. The shampoo composition of claim 1, wherein the anionic emulsifier is selected from the group consisting of: Poly(meth)acrylic acid; copolymers of (meth)acrylic acids and its (meth)acrylates with C1-C22 alkyl; copolymers of (meth)acrylic acids and (meth)acrylamide; and mixtures thereof.

5. The shampoo composition of claim 1, wherein the anionic charged polyacrylate microcapsule has a particle size of from about 2 microns to about 80 microns.

6. The shampoo composition of claim 1, wherein the polyacrylate microcapsule has a core and a shell that encapsulates said core.

7. The shampoo composition of claim 6, wherein the core comprises from about 6% to about 99.9% of a benefit agent.

8. The shampoo composition of claim 7, wherein the benefit agent is selected from the group consisting of perfumes; brighteners; enzymes; sensates; attractants; dyes; pigments; bleaches; anti-dandruff agents; and mixtures thereof.

9. The shampoo composition of claim 8, wherein the anti-dandruff agent is ZPT.

10. The shampoo composition of claim 1, wherein the cationic deposition polymer is a synthetic polymer or a naturally derived cationic polymer derived from the group consisting of starches, guar, cellulose, cassia, locust bean, Konjac, Tara, galactomanna, and Tapioca starch.

11. The shampoo composition of claim 1, wherein the cationic deposition polymer is a water-soluble polymer with a charge density of from about 0 5 milliequivalents per gram to about 12 milliequivalents per gram, and wherein the cationic deposition polymer has a molecular weight of about 100,000 Daltons to about 5,000,000 Daltons.

12. The shampoo composition of claim 1, wherein the detersive surfactant is anionic, zwitterionic, amphoteric, and combinations thereof.

13. The shampoo composition of claim 1, wherein the carrier comprises either water or water solutions of lower alkyl alcohols and polyhydric alcohols.

14. The shampoo composition of claim 1, wherein the anionic charged polyacrylate microcapsule is contained in an agglomerate, and wherein the agglomerate comprises materials selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof.

15. The shampoo composition of claim 1, wherein the shampoo composition is in the form of a gel, and wherein the gel comprises less than about 45% water.

16. The shampoo composition of claim 15, wherein the gel has a neat viscosity of about 1,000 cps to about 10,000 cps.

17. A method of making a shampoo composition, said method comprising:
    a) coating a polyacrylate microcapsule with an anionic emulsifier to form an anionic polyacrylate microcapsule;
    b) combining the anionic polyacrylate microcapsule with a cationic deposition polymer to form a premix;
    c) adding the premix to a detersive composition comprising surfactant and a carrier.

18. A method of making a shampoo composition, said method comprising:
    a) coating a polyacrylate microcapsule with an anionic emulsifier to form an anionic polyacrylate microcapsule;
    b) combining the anionic polyacrylate microcapsule with a cationic deposition polymer to form a premix;
    c) adding the premix to a anionic surfactant;
    d) adding the resulting mixture of step (c) to a detersive composition comprising surfactant and a carrier.

19. The method of making a shampoo composition of claim 18, wherein the anionic surfactant is selected from the group consisting of alkyl and alkyl ester sulfates, and the water soluble salts of organic, and sulfuric acid reaction products.

* * * * *